United States Patent
David

(10) Patent No.: US 7,460,975 B2
(45) Date of Patent: Dec. 2, 2008

(54) METHOD OF SENSING THE MOTION OF A SOLID, USING AN ABSOLUTE MEASUREMENT THAT IS ASSOCIATED WITH A MEASUREMENT CALCULATED BY DOUBLE INTEGRATION

(75) Inventor: Dominique David, Claix (FR)

(73) Assignee: Commissariat a l'Energie Atomique, Paris (FR)

( * ) Notice: Subject to any disclaimer, the term of this patent is extended or adjusted under 35 U.S.C. 154(b) by 0 days.

(21) Appl. No.: 10/582,764

(22) PCT Filed: Dec. 20, 2004

(86) PCT No.: PCT/FR2004/050729

§ 371 (c)(1),
(2), (4) Date: Jun. 13, 2006

(87) PCT Pub. No.: WO2005/064271

PCT Pub. Date: Jul. 14, 2005

(65) Prior Publication Data

US 2007/0163343 A1    Jul. 19, 2007

(30) Foreign Application Priority Data

Dec. 22, 2003    (FR)    ................................ 03 51167

(51) Int. Cl.
*G01P 3/00*    (2006.01)
*G06F 15/00*    (2006.01)
(52) U.S. Cl. ..................................... 702/145; 702/150
(58) Field of Classification Search ................. 702/141, 702/145, 150–154
See application file for complete search history.

(56) References Cited

U.S. PATENT DOCUMENTS

| 4,119,212 | A | 10/1978 | Flemming | 414/5 |
| 5,645,077 | A | 7/1997 | Foxlin | 600/587 |
| 5,819,206 | A | 10/1998 | Horton et al. | 702/150 |
| 2003/0028340 | A1 | 2/2003 | Brunstein | 702/94 |
| 2003/0045998 | A1 | 3/2003 | Medl | 701/207 |
| 2003/0047002 | A1 | 3/2003 | Arms | 73/504.17 |
| 2007/0123806 | A1 | 5/2007 | Bouvier et al. | |
| 2007/0163343 | A1 | 7/2007 | David | |

FOREIGN PATENT DOCUMENTS

| EP | 0 655 301 | | 5/1995 |
| EP | 1 310 770 | | 5/2003 |
| FR | 2 838 185 | | 10/2003 |
| FR | 2 847 689 | | 5/2004 |
| WO | 2007/093641 | * | 8/2007 |

OTHER PUBLICATIONS

Answers.com Dictionary, printed Feb. 20, 2008.*

* cited by examiner

*Primary Examiner*—Michael P Nghiem
(74) *Attorney, Agent, or Firm*—Oblon, Spivak, McClelland, Maier & Neustadt, P.C.

(57) ABSTRACT

A method for measuring movement of a solid, using an absolute measurement associated with a double integration measurement. The method can be applied in particular to sensing movements of the human body and includes a series of measurement of the acceleration of the solid and double integration of the measurements to obtain successive values of a first translation of the solid, and a series of absolute measurements of at least one second degree of freedom of the solid, namely a rotation, and this measurement of rotation is converted into a measurement of translation used to update the first translation.

9 Claims, 1 Drawing Sheet

METHOD OF SENSING THE MOTION OF A SOLID, USING AN ABSOLUTE MEASUREMENT THAT IS ASSOCIATED WITH A MEASUREMENT CALCULATED BY DOUBLE INTEGRATION

TECHNICAL AREA

The present invention relates to a method for measuring—the term <<sensing>> also being used—the movement of an object or, more precisely, of a solid, i.e. measuring the movements of this solid.

It is recalled that any movement of a solid entails a translation and a rotation (but can be limited to mere translation of mere rotation).

The invention particularly applies to sensing movements of the human body.

It therefore finds applications, for example, in the areas of sports, medicine, cinema, multimedia and Augmented Reality.

With the invention it is possible to sense a movement reliably and at low cost, even the rapid movement of a person.

STATE OF THE PRIOR ART

Reference is made to the following document:

[1] WO 03/085357A, international application n° PCT/FR03/01025, filed on 2 Apr. 2003, <<Device for Rotational Motion Capture of a Solid>>, invention by Dominique David and Yanis Caritu.

The invention completes the technique described in document [1] which uses a device called an <<attitude control system>>, comprising at least one angle position sensor (preferably at least one accelerometer and at least one magnetometer). With the invention it is possible to increase the performance of this technique, in particular for rapid movements.

Various techniques are known, having greater or lesser performance characteristics, to determine the movement of a mobile object. In particular, the double integration method is known which uses acceleration measurements made by means of one or more accelerometers.

This double integration method is implemented in positioning systems called <<inertial systems>> and gives good results even for rapid movements, or more precisely movements of rapidly varying speed. However the double integration of signals provided by accelerometers is a source of positioning drift.

To limit this drift, in particular in the aviation or space sector, high performance accelerometers have come to be used which are unfortunately very costly.

Also, an absolute measurement method is known to measure a movement using one or more accelerometers and one or more magnetometers. This method does not cause drift but can only be used to measure the movement of an object whose speed varies slowly.

DESCRIPTION OF THE INVENTION

The purpose of the present invention is to overcome the drawbacks of known methods for measuring the movement of a solid, mentioned above, namely the absolute measurement method and the double integration method, with a view to obtaining a method which is not a source of position drift and can be implemented to study movements with fast speed variation.

According to one particular aspect of the invention, the double integration method and the absolute measurement method are combined in order to update the measurements provided by the double integration method using the measurements provided by the absolute measurement method, these latter measurements being taken into account when the solid whose movement is being measured slows downs or more precisely when the speed of this solid varies slowly.

More specifically, the subject of the present invention is a method for measuring the movement of a solid, a method in which at least a first translation of this solid is measured (first degree of freedom), this method comprising a series of steps of measurement of the acceleration of the solid and double integration of the measurements thus made in order to obtain successive values of the first translation, this method being characterized in that it also comprises a series of absolute measurement steps to measure at least one second degree of freedom of the solid, this second degree of freedom being a rotation, using at least one rotation sensor, and in that this rotation measurement is converted into a translation measurement and this translation measurement is used to update the first translation.

In the present invention, the measurement of the second degree of freedom, obtained at this step, can be used as initial condition to obtain, by double integration, the value of the first translation which follows after the previously obtained values of this first translation.

In the present invention, the steps of absolute measurement and the steps of measuring the acceleration of the solid may be simultaneous, each absolute measurement step therefore occurring at the same time as a measurement step of the acceleration of the solid.

Preferably, the conversion of the rotational measurement into a translation measurement uses kinetic models of the solid and/or of its movement, so that relationships between rotation and translation can be determined.

The rotation sensor is preferably chosen from among accelerometers and magnetometers (hence the second degree of freedom is measured using at least one accelerometer and/or at least one magnetometer).

According to one particular embodiment of the invention, the first translation is measured using a translation sensor which is also the rotation sensor.

Preferably, a criterion of slowness of movement is chosen (more precisely a criterion of slow variation in the speed of the solid) and, if the movement meets this criterion after one of the steps measuring the second degree of freedom, the measurement of the second degree of freedom obtained at this step is used to update the first translation.

The criterion of slowness of movement may be the lying of a function of the acceleration norm of the solid below a predetermined threshold.

This function may be this norm itself.

BRIEF DESCRIPTION OF THE DRAWINGS

The present invention will be better understood on reading the following description of examples of embodiment given solely for indication purposes and in no way restrictive, with reference to the appended drawings in which.

DETAILED DESCRIPTION OF PARTICULAR EMBODIMENTS

Figure 1:
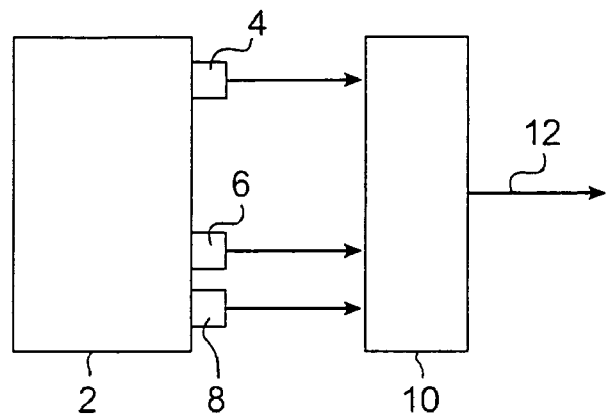
FIG. 1 schematically illustrates a device for implementing an example of the method that is the subject of the invention, and FIGS. 2 et 3 schematically illustrate examples of the invention.

In one example of the invention, it is sought permanently to determine the position of an object, more precisely of a solid, by measuring the values of the six degrees of freedom of this solid.

The attitude control device described in document [1] enables measurement of the three angular degrees of freedom of the solid. The present invention makes it possible to complete this known device with an inertial device which therefore extends the capabilities thereof.

One originality of the present invention lies in the type of coupling it proposes, namely a technique using an absolute sensor and a technique using an inertial sensor.

The absolute sensor is the attitude control unit which provides absolute measurements on the angle positioning of the solid. These measurements are accurate when the solid is at rest; but they become flawed with errors when the solid undergoes accelerations, the errors being greater the stronger the acceleration.

The inertial sensor consists of one or more accelerometers whose precision is as high as possible. Possibly, it is possible to use three accelerometers each having an axis of sensitivity, the respective axes of sensitivity being orthogonal two by two, or one accelerometer having three axes of sensitivity, orthogonal two by two.

The method of measurement is as follows:

The translation data of the solid are calculated by double integration of the signals provided by the accelerometer(s), and the rotation data are calculated from the attitude control unit.

This attitude control unit is able to determine whether the movement in progress is rapid or slow, and hence if the values it provides are accurate or distorted, e.g. by evaluating the absolute value of the amplitude of the measurements provided by the accelerometer(s) contained in the attitude control unit.

In slow movement phases, the data of this attitude unit is used to update the movement of the solid.

In phases of rapid movement, the output signals of the accelerometer(s) (which are preferably high precision accelerometers) are integrated twice and therefore provide a more accurate answer than the answer given by the attitude unit.

It is to be noted that this method does not cover the sensing of movements in its general entirety. On the other hand, it ideally covers the sensing of movements of the human body, and more generally the body of a vertebrate, even an assembly of mechanically jointed rigid segments. In some cases, this method can also be applied when an a priori model of the movement of the solid is known, e.g. for ballistic movement.

Regarding the human body, the complete posture of the body is known through a conjunction of attitude control systems arranged on the bone segments. This measurement is flawed with errors in the event of rapid body movements.

One method conforming to the invention then consists of using double integration during phases in which body movements are rapid (these phases generally being short, since the body is only able to make periodic movements) and of changing to update mode whenever accelerations of body movements become low.

FIG. 1 is a schematic view of a device for implementing a method conforming to the invention.

This device makes it possible to measure the movement of a solid 2 and comprises:

one or more accelerometers 4, one or more accelerometers 6 and/or one or more magnetometers 8, and electronic means 10 provided to store and process, according to the invention, the data or signals provided by the accelerometer(s) 4 and accelerometer(s) 6 and/or the magnetometers 8, and to store the results of processing.

The accelerometer(s) 4 and accelerometer(s) 6 and/or magnetometer(s) 8 are attached to the solid 2 whose movement is to be measured. The electronic means 10 may or may not be joined to this solid 2.

The electronic means 10 are therefore provided to implement the invention by cooperating with the accelerometer(s) 4 and accelerometer(s) 6 and/or with the magnetometer(s) 8.

In particular, they cooperate with the magnetometer(s) 4 to implement a double integration measurement method, and with the accelerometer(s) 6 and/or the magnetometer(s) 8 to implement an absolute measurement method.

In FIG. 1, reference 12 denotes an output of the electronic means 10, in which the processing results can be recovered e.g. for the display of these results.

Examples of the invention are considered below in which joint use is made of angle data and accelerometric data.

The first example relates to a permanent updated double integration.

Each measurement point is equipped with a set of sensors, comprising 1 to 3 accelerometers and possibly 1 to 3 magnetometers.

When three accelerometers are used each having an axis of sensitivity, they are advantageously arranged so that their respective axes of sensitivity form a trirectangular trihedron.

The same applies if three magnetometers are used each having an axis of sensitivity.

In this first example, the acceleration data are permanently integrated twice. The output signals obtained therefore result from this double integration. However, it is known that this double integration is subject to drift, whose amplitude depends upon the quality of the accelerometer(s) used.

To overcome this disadvantage, according to the invention, permanent and parallel acquisition is made of the data from the angle control system [accelerometer(s) and possibly magnetometer(s)].

A quality index of this angular data is also calculated. This is a function of the norm $\|a\|$ of the acceleration vector relative to the norm of the acceleration g of gravity, measured at rest, a function which may for example be the ratio $\|a\|/\|g\|$.

This quality index is used as a criterion for slowness of movement or, more precisely, slowness in the speed variation of this movement.

When the movement is sufficiently slow, which is determined for example by comparing this index with a predetermined threshold and by determining whether this index is lower than this threshold, the angle data are then used to calculate a position resulting from the movement of the solid under examination.

This position is then used as starting position for the following double integration period.

If the movement remains practically static, an update is made after a time interval determined by the accuracy which is expected from the measurements, so that the estimate of the drift resulting from double integration remains lower than the required accuracy within this time interval.

Figure 2:
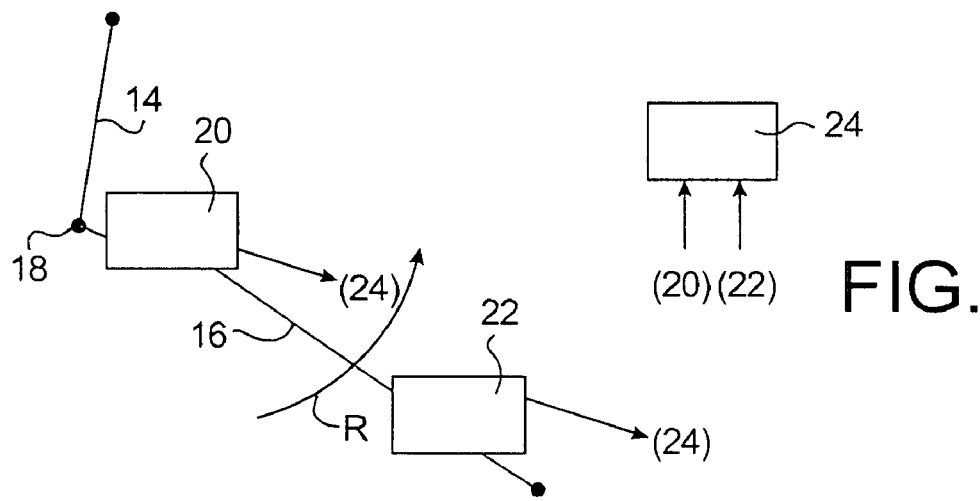

The second example, described referring to FIG. 2, relates to a so-called <<variable lever arm>> method.

FIG. 2 shows two rigid parts 14 and 16 which are jointed using any appropriate means 18. For example, part 14, part 16 and their joint 18 are respectively an arm and the corresponding forearm and elbow.

According to the invention, the forearm 16 is equipped with two assemblies 20 and 22 distant from each other.

Each assembly comprises one to three accelerometers and forms a measurement point. If it comprises three accelerometers, these are mounted so that their axes of sensitivity form a trirectangular trihedron. At least one of the two measurement points 20 and 22 also comprises three magnetometers whose axes of sensitivity form a trihedron that is advantageously trirectangular.

During a rotational movement of the forearm 16, of the type symbolized by arrow R in FIG. 2, the two assemblies 20 and 22 record different accelerations since the acceleration recorded by one assembly depends upon its distance from the centre of rotation, namely the elbow 18 in this example.

The difference in accelerations is used to evaluate the acceleration component after eliminating the contribution made by gravity.

The estimate of this measurement is then used for the calculation of the rotation angles (see document [1]) by subtraction from total acceleration, as measured by one of the two assemblies which is accordingly provided with 6 sensors (three accelerometers and three magnetometers). This gives access to an angle measurement that is rid of the disturbance due to a rapid movement.

All these calculations are made in electronic processing means 24 which receive the signals provided by sensors 20 and 22.

The third example relates to the use of a movement model.

This third example is based on the fact that some movements are very limited regarding the number of degrees of freedom. For example, in the human body, a thigh is practically limited to only one degree of freedom of rotation during walking and running phases.

In this case, the movement under consideration may be described by a single parameter, even a single value of this parameter. The maximum value of measured acceleration can therefore give information on the entire rotation.

The above considerations are based on physiological studies determining such results.

The method of the invention used in this third example is therefore the following.

Knowing a starting position that is easily identifiable since it concerns either a stop position or a return path of rotation or translation, the maximum value of the acceleration vector norm is measured in the following phase, by means of three sensors whose axes of sensitivity form a trirectangular trihedron, until a new characteristic step is identified and known.

This set of data is used to extract the parameter required for qualifying the whole movement. This step is no longer conducted in real time since it requires knowledge of the whole movement, but with a (slight) time shift.

Other examples of the invention are given below.

It is recalled firstly that the techniques for measuring movement, which are based on inertial sensors, all suffer from the same defect, namely measurement drift caused by double integration of noises of various origins (in particular electronic noises and physiological noises), these noises being added to the signal to be measured.

Under one aspect of the present invention, this problem is solved using a technique based on a device known from document [1], with which it is possible to obtain absolute measurement of angles using angle position sensors and magnetic field sensors.

The originality of this technique lies in the use of the three following operating modes:
- absolute measurement of angles using one or more accelerometers and/or one or more magnetometers,
- use of behavioral models (see the example of the human body given below), enabling the absolute measured angles to be related to effective translations in space of the mobile solid (e.g. a hand), and
- calculation of movements by double integration of the signals derived from the accelerometers which preferably have high precision.

With the combined use of these three operating modes it is also preferable to add a suitable method for merging the collected data, which is described below.

This method is similar to the data merging method described in document [1]. The complexity of this case is due to the fact that a sufficiently rapid movement is permitted which adds an acceleration component that is superimposed on gravity. This acceleration component adds 3 additional unknowns (along the 3 axes). But the high precision accelerometers also provide an additional data item.

The algorithm is the following:
(a) as movement status, the status calculated in the preceding step is used (position, speed, acceleration),
(b) this is used to deduce expected measurement values at the sensor outputs,
(c) using a conventional mathematical optimization method (e.g. the gradient descent method or similar more recent methods) the initial status values of movement are corrected, and
(d) return to step (a) until the estimated values at the sensor outputs are sufficiently close to actual measured values.

An example of the invention is given below relating to the sensing of movements of the human body, having six degrees of freedom.

Figure 3:
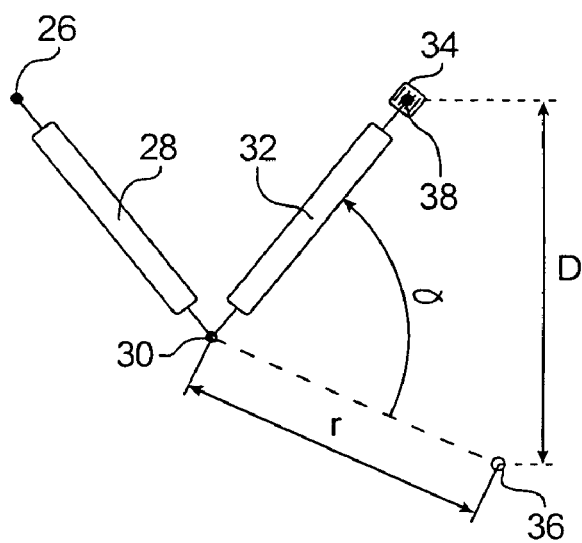

This example is schematically illustrated FIG. 3. Here it is limited to the arm, but can be generalized to the whole body.

In FIG. 3, references 26, 28, 30, 32 and 34 respectively represent the shoulder, arm, elbow, forearm and hand.

The initial and final positions of the hand are respectively referenced 36 and 38.

The movement of the hand, which makes a vertical translation of amplitude D, translates as a rotation of angle $\alpha$ about the elbow and possibly, depending upon the amplitude of the translation, by another rotation about the shoulder.

Instead of directly measuring D, it is therefore possible to measure $\alpha$. Knowing the length r of the forearm, its amplitude D of translation can be deduced.

This technique in accordance with the invention has the advantage of being based solely on absolute measurements: it is therefore devoid of any drift.

It is to be noted that this technique uses, inter alia, one or more accelerometers (attached to the forearm but not shown) to measure angle $\alpha$. This assumes that said sensors measure gravity and their respective angle positions can therefore be known with respect to the vertical.

In the event of a rapid movement, the accelerometer(s) also measure the acceleration resulting from said movement, which means that the angle measurement is distorted.

A technique known from document [1] can be used to solve this problem in part.

It consists of reducing the contribution made by the accelerometer(s) to the benefit of the magnetometer(s) when calculating the angle or angles. But this technique is only partly efficient and is dependent upon the movement made.

A technique put forward in the present invention is capable of completing the previous technique and is not limited by the type of permitted movement.

This technique is set forth below.

As soon as a rapid movement is detected (for which all that is required is to calculate the norm of the acceleration vector):

the movement of the sensor is calculated by double integration taking as starting point the status of the mobile solid (the forearm in the example) at the start of the rapid phase, simultaneously, any drift is corrected by merging the magnetometric data, and as soon as the movement slows down, absolute mode is resumed.

In this manner any drift can be eliminated which may have occurred during the integration phase.

The merging of the magnetometric data consists, conjointly with double integration, of using an estimate of the rapid movements using the magnetometers alone. This latter technique was described above (reducing the contribution by the accelerometer(s) to the benefit of the magnetometer(s) when calculating the angle or angle(s)).

Firstly, the double integration theoretically provides the complete movement, but it is subject to drift.

Secondly, the magnetometers provide a partial estimate (excluding rotations about the axis of the earth's field) but not subject to drift.

One possible merging consists of estimating the movement from double integration, deducing estimated magnetic measurements therefrom, and using the difference between the latter and actual magnetic measurements to correct the estimated movement using a technique of gradient descent type.

In addition, a merger algorithm can be used between the double integration method and the absolute measurement method, by changing from one to the other not in discontinuous fashion but gradually by progressively reducing the absolute contribution of the accelerometers and progressively increasing the influence of double integration when the movement accelerates, and conversely during the deceleration phase.

To do so (gradual reduction and increase) the procedure may be as described below.

The status of the mobile is estimated (position, speed, acceleration) from the last known status and from the double integration of the high precision accelerometers. These are used to deduce estimates of magnetometric and accelerometric data of the system for absolute measurement of angles (attitude control system). The distance between these estimates and actual measurements is calculated. The estimated movement is corrected by applying a method of gradient descent type.

The correction under consideration is parametered: it is greater the slower the movement, the criterion being for example the ratio of the norm of the acceleration vector to the norm of g, this ratio being mentioned above.

Therefore, a very slow movement does not use the data derived from the double integration, whilst a very rapid movement exclusively uses this data.

The invention has all the advantages of the technique described in document [1]:

it can be implemented at low cost, it does not require any external equipment, such as magnetic sources or cameras, and it can be implemented using robust algorithms.

In addition, the invention leads to reliable measurements even for rapid movements.

Also, the present invention can be implemented with an attitude control system whose angle accuracy is 1° or lower and with accelerometers having at least 10 bits (advantageously 14 to 16 bits).

It is specified that the above-mentioned criterion of <<slowness of movement>> is related to the movement accuracy it is desired to achieve. One purpose of the invention being to separate acceleration of the solid from acceleration of gravity, for as long as the acceleration norm of the solid remains less than $$\frac{1}{10}$$

$\|g\|$ (scarcely different from $1m/s^2$), the movement will be considered as slow and the method will lead to acceptable accuracy.

The invention claimed is:

1. A method for measuring movement of a solid, in which at least one first translation of the solid is measured, the method comprising:

a series of measuring acceleration of the solid and making double integration of the measurements, to obtain successive values of the first translation;

a series of absolute measurement of at least one second degree of freedom of the solid, the second degree of freedom being a rotation, by at least one rotation sensor;

converting the measurement of rotation into a measurement of translation; and using the translation measurement to update the first translation, wherein a criterion of slowness of movement is chosen, and when the movement meets this criterion after one of the measurements of the second degree of freedom, the measurement of the second degree of freedom obtained is used to update the first translation.

2. A method as in claim 1, wherein the measurement of the second degree of freedom is used as an initial condition to obtain by double integration a value of the first translation that follows previously obtained values of the first translation.

3. A method as in claim 1, wherein each absolute measurement is made at a same time as a measurement of the acceleration of the solid.

4. A method as in claim 1, wherein the converting the measurement of rotation into a measurement of translation uses kinetic models of the solid and/or of movement of the solid, enabling determination of relationships between the rotation and translation.

5. A method as in claim 1, wherein the rotation sensor is chosen from among accelerometers and magnetometers.

6. A method as in claim 1, wherein the first translation is measured using a translation sensor that is also the rotation sensor.

7. A method as in claim 1, wherein the criterion of slowness of movement is lying of a function of an acceleration norm of the solid below a predetermined threshold.

8. A method as in claim 7, wherein the function of the acceleration norm of the solid is the norm itself.

9. A method as in claim 1, wherein the first translation of the solid is measured by means of an acceleration sensor which measures all accelerations, in particular the acceleration caused by gravity, and the thus measured acceleration of gravity is suppressed to determine the acceleration of the solid.

* * * * *